(12) United States Patent
Aarts et al.

(10) Patent No.: US 11,930,803 B2
(45) Date of Patent: Mar. 19, 2024

(54) PROCESSING OF INSECT LARVAE

(71) Applicant: Bühler Insect Technology Solutions AG, Uzwil (CH)

(72) Inventors: Kees Wilhelmus Petrus Aarts, Vught (NL); Maurits Petrus Maria Jansen, Bavel (NL); Anne Louise Mia Jacobs, Dongen (NL); Mark C. Mescher, Zurich (CH); Robert Prentner, Zollikon (CH); Alexander Mathys, Zurich (CH); Consuelo M. de Moraes, Zurich (CH)

(73) Assignee: Bühler AG, Uzwil (CH)

( * ) Notice: Subject to any disclaimer, the term of this patent is extended or adjusted under 35 U.S.C. 154(b) by 309 days.

(21) Appl. No.: 15/734,247

(22) PCT Filed: Jun. 5, 2019

(86) PCT No.: PCT/EP2019/064672
§ 371 (c)(1),
(2) Date: Dec. 2, 2020

(87) PCT Pub. No.: WO2019/234106
PCT Pub. Date: Dec. 12, 2019

(65) Prior Publication Data
US 2021/0212307 A1    Jul. 15, 2021

(30) Foreign Application Priority Data
Jun. 5, 2018   (EP) .................................... 18175914

(51) Int. Cl.
*A01M 1/00*   (2006.01)
*A01M 1/20*   (2006.01)
*A22B 7/00*   (2006.01)

(52) U.S. Cl.
CPC ........... *A01M 1/2094* (2013.01); *A22B 7/008* (2013.01)

(58) Field of Classification Search
CPC ............................ A01M 1/2094; A22B 7/008
(Continued)

(56) References Cited

U.S. PATENT DOCUMENTS

| 5,866,317 A | 2/1999 | Miyazawa et al. |
| 2003/0124199 A1 | 7/2003 | Nietsch et al. |

(Continued)

FOREIGN PATENT DOCUMENTS

| CN | 102026555 A | 4/2011 |
| JP | 2008519855 A | 6/2008 |

(Continued)

OTHER PUBLICATIONS

EFSA Scientific Committee, "Risk profile related to production and consumption of insects as food and feed: Risk profile of insects as food and feed", EFSA Journal, 2015, pp. 1-60, vol. 13:10.

(Continued)

*Primary Examiner* — Richard T Price, Jr.
(74) *Attorney, Agent, or Firm* — The Webb Law Firm

(57) ABSTRACT

The present invention provides a method and system for processing insect larvae in an ethical manner and without imposing unnecessary stress on them. The method involves anaesthetising the insects by cooling and then cutting them, thereby destroying the nervous system of the insects. Thus, an energy-saving method of processing insects with minimal stress is provided.

18 Claims, 1 Drawing Sheet

(58) Field of Classification Search
USPC .......................................................... 452/66
See application file for complete search history.

(56) References Cited

U.S. PATENT DOCUMENTS

| | | | |
|---|---|---|---|
| 2008/0075818 A1 | 3/2008 | Papadoyianis et al. | |
| 2011/0045141 A1 | 2/2011 | Natori et al. | |
| 2018/0103679 A1 | 4/2018 | Leo | |

FOREIGN PATENT DOCUMENTS

| | | | | |
|---|---|---|---|---|
| JP | 2010006711 A | | 1/2010 | |
| KR | 2010053349 A | * | 5/2010 | ........... G06F 3/0412 |
| RU | 2151503 C1 | | 6/2000 | |
| WO | 9526633 A2 | | 10/1995 | |
| WO | 199848617 | | 11/1998 | |
| WO | 03013557 A1 | | 2/2003 | |
| WO | 2006053253 A2 | | 5/2006 | |
| WO | 2009139346 A1 | | 11/2009 | |
| WO | 2013191548 A1 | | 12/2013 | |

OTHER PUBLICATIONS

Stamer, "Insect proteins—a new source for animal feed: The use of insect larvae to recycle food waste in high-quality protein for livestock and aquaculture feeds is held back largely owing to regulatory hurdles", EMBO reports, 2015, pp. 676-680, vol. 16:6.
Entomo, "[Insect food] Japanese version of cricket bread and mealworm hamburger," Jan. 17, 2018, https://entomo.jp/blog/cricket-bread-mealworm-hamburg01.html (English translation provided).
NewSphere, "Larva burger released in Switzerland Cricket, grasshopper, worm sales lifted," Oct. 21, 2017, https://newsphere.jp/culture/20171021-1/ (English translation provided).
Wired, "What is a design that gives a sense of security to 'insect dishes'?" May 29, 2014, https://wired.jp/2014/05/29/insect-factory/ (English translation provided).

* cited by examiner

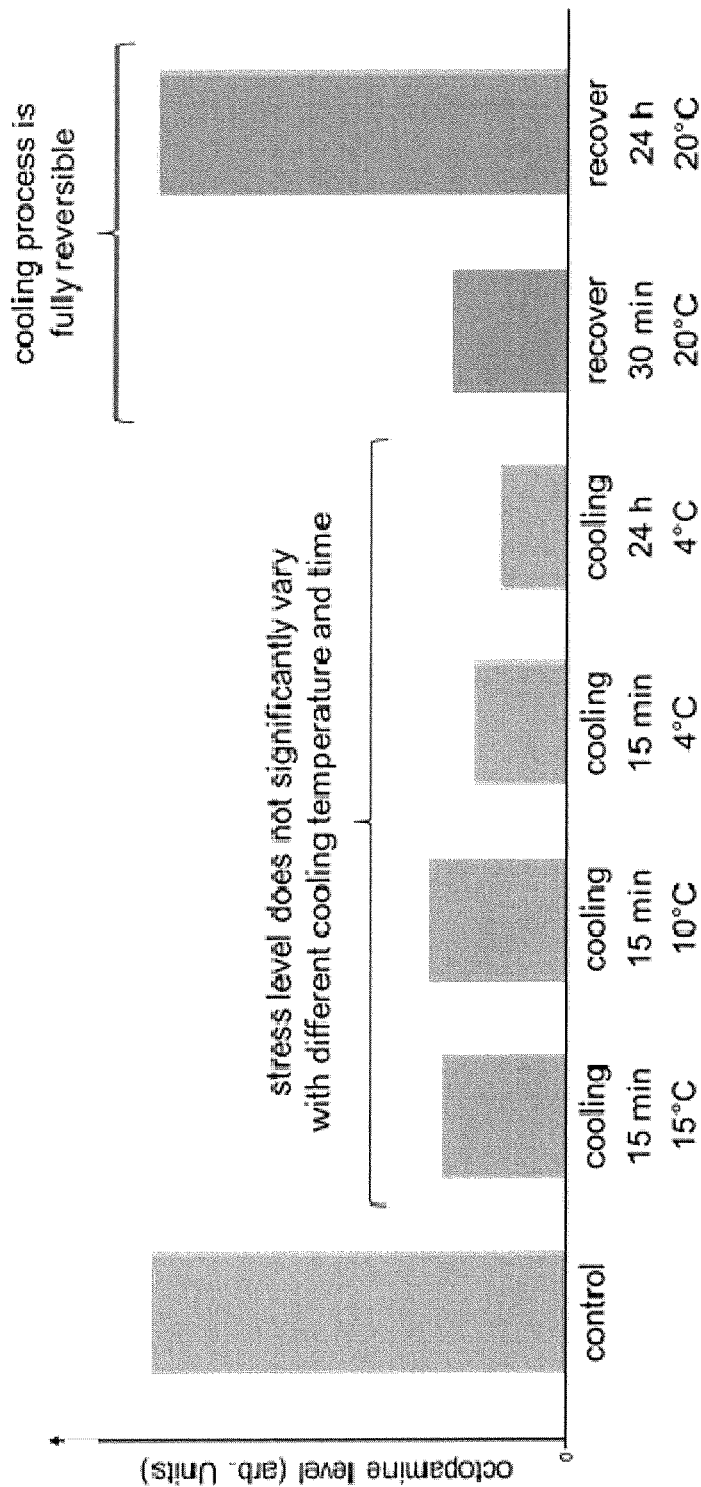

PROCESSING OF INSECT LARVAE

CROSS-REFERENCE TO RELATED APPLICATIONS

This application is the United States national phase of International Application No. PCT/EP2019/064672 filed Jun. 5, 2019, and claims priority to European Patent Application No. 18175914.3 filed Jun. 5, 2018, the disclosures of which are hereby incorporated by reference in their entirety.

BACKGROUND OF THE INVENTION

Field of the Invention

The invention generally relates to processing of insect larvae in a most appropriate way regarding ethics, involving anaesthetising and inactivating the insect larvae with minimal stress implications.

Discussion of the Related Art

The use of insects as a food source for humans and livestock has significant potential to meet increasing demands imposed by ongoing human population growth and to address concerns about sustainability and long-term food security. However, large scale production and harvesting of insects gives rise to ethical questions pertaining to animal-welfare.

There are different approaches to handle larvae before and during the inactivation step involving drying, boiling, freezing, mincing or gassing. It is, however, still under discussion which methods are the most suitable for not causing unnecessary stress while still facilitating large scale processing.

Currently the state-of-the-art technology to inactivate insects is freezing, which is a cost-intensive process. Other methods include flash freezing, dry-freezing, drying, boiling or gassing the insect larvae. Generally, the dead insects are then treated by grinding or cutting and processed to protein powder. By applying cooling-cutting, insect inactivation by destruction of the nervous system without putting additional stress to the insects can be achieved. Other techniques involving heat such as drying or boiling and cutting without anaesthetising increase stress levels in insects or, e.g. $CO_2$ gassing, are not as fast as the proposed method.

WO 2013/191548 A1 describes a method of converting insects or worms into nutrient streams, the method comprising a first step of squashing the insects to obtain a pulp.

US 2008/0075818 A1 discloses a method of producing high protein insect meal as animal feed. Therefor, the insects are dried and, after thorough desiccation, ground into meal. Drying however, as well as freezing, is a slow process and highly energy-intensive.

Thus it is an objective of the present invention to provide an efficient method of processing insect larvae without imposing unnecessary stress on them.

SUMMARY OF THE INVENTION

According to the invention, a method is proposed which comprises cooling the insects in order to anaesthetise them and destroy their nervous system by means of cutting resulting in inactivation of the insects.

The cooling may be performed by adding a fluid, e.g. cold water. The fluid/insect larvae mixture may have a ratio of 50:50 or may have any other suitable ratio, such as between 30:70 and 80:20.

The target temperature of the cooling process is 15° C. or lower.

The target temperature of the cooling process may be 10° C., 7° C. or lower. The cooling medium used in the cooling process is preferably liquid. In case of water, the temperature is thus preferably maintained above 0° C.

The cutting process may cut each insect larva in at least 5 or preferably 10 pieces in a very short time. Preferably, at least 90% of the larvae are cut.

The insect larvae may be processed to powder comprising protein and/or fat and/or chitin. The insect larvae to be treated preferably are black soldier fly larvae or meal worms. The insect larvae are preferably suitable for producing animal feed or food.

The processing of the larvae according to the invention preferably involves cooling, separating and inactivation of the insect larvae. Specifically, the insect larvae may be separated from rearing residue before being processed. The separation step or washing step can thereby be performed using a fluid, e.g. water, gas or mechanical means.

Additionally, the insect larvae may be stored in cold water before being sent to processing. The storing may be performed in tanks. Preferably during storage, the amount of water in the water-larvae mixture is between 30-80% by weight. During storage, the water may have a temperature below 15° C. in order to metabolically deactivate the insect larvae, which can be considered as an anaesthetising step. Also, storage in a cold environment helps preventing contamination with and growth of microbial pathogens. Furthermore, since they float in water, crushing of the larvae due to their own weight can be prevented. The temperature may preferably be below 7° C. Also, the water/insect larvae mixture may be agitated by agitating means in order to provide a homogenous cooling. In that way, the insect larvae can be stored for a period of up to four days.

The features, objects and advantages of the invention will be made apparent by the detailed description and the accompanying drawing.

BRIEF DESCRIPTION OF THE DRAWING

FIG. 1 shows the stress level of insect larvae in response to different stimuli.

DETAILED DESCRIPTION OF THE INVENTION

In order to assess the stress level of insect larvae during rearing and processing, research has been done to identify a way to inactivate insects with minimal stress levels.

Stress might correlate to the various steps in processing such as anaesthetising, washing, transport, storage, and inactivation of larvae. The presence of potentially stressful conditions was assessed by measuring physiological responses to the corresponding stimuli.

To assess physiological response to stress, levels of the stress-related hormone Octopamine (OCT) was measured. In invertebrates, Octopamine regulates muscle activity and flight-or-fight behavior. Concentrations of Octopamine can be used as proxy for physiological responses to stressful conditions. After exposing larvae to various stimuli, increases or decreases in OCT are measured relative to unexposed control larvae.

In the course of the research, the following stimuli were tested:
  Chilling of the larvae for 5-15 minutes at 4-15° C., immersed in water.

Exposure to heat without inducing permanent damage to the insect larvae

Storage in a 50:50 mixture of water/larvae at 4° C. and 10° C.

Gassing the larvae with $CO_2$.

Abruptly cooling the insect larvae by immersing them in water of 4° C. immediately rendered the major part of the insect larvae immobile. The OCT level thereby decreased and did not rise back to the control level measured before the treatment while being chilled. After exposing the insect larvae to room temperature, the OCT level again reached the control level. As an aside it has to be noted, that OCT level does not always correlate with visible behaviour, rendering OCT a more reliable indicator for relaxation/arousal.

Exposure to severe heat, but without effectively harming the insect larvae, lead to curling behaviour which is considered as being painlike behaviour. The heat exposure clearly resulted in increased OCT levels indicating that any method involving heat without prior anaesthetising or inactivation of larvae should be avoided.

Spraying with water did not result in any visual behavioural response of the larvae.

Two stimuli that most likely have an anaesthetic effect on larvae were investigated: Chilling larvae in cold water and gassing larvae with $CO_2$. Putting larvae into cold water of 4° C. instantly rendered most larvae immobile and no movement was observed after one minute. After 10 minutes, larvae were removed from the water and put on a dry surface. From there on, the time was recorded until larvae exhibited visible signs of activity. Onset of movement was visible after approximately 5 minutes, and normal movement was recovered after approximately 12 minutes.

Due to the fact that insects are poikilothermic, for anaesthetising the insect larvae and stopping their metabolism, temperatures of 15° C. or less, preferably 10° C. or less, are sufficient. Cooling has no effect on the animals' physiology and they can be stored up to 4 days and reactivated if desired without causing any harm.

When being gassed with $CO_2$, on the other hand, movement was slowly beginning to decrease only after approximately 2 minutes with widespread loss of movement only after around 8 minutes of exposure. After 10 minutes, treatment was stopped and larvae were put again on a dry surface. First slow movements already set in after 1-2 minutes, and after 5 minutes, normal behaviour was recovered. These qualitative findings indicate, first, that chilling using cold water is more effective in anaesthethising larvae compared to gassing, and secondly, recovery after chilling is slower than after gassing.

While the above described research was focused on non-lethal stimuli, in further evaluations, different processing methods were assessed. Those involved cutting, boiling and ripping with the use of heat. Consequently, the curling or escape behaviour after the lethal process was observed. With reference to table 1 it was thereby noticed that cutting lead to a very weak response, boiling induced a medium response and heat ripping caused a strong or long lasting curling behaviour in more cases compared to the other processing methods. Hence, inactivation methods that involve heat are comparatively slow and tend to increase response intensity, while methods using an effective cutting technique are recommended for processing purposes. Methods involving gassing of the animals are acceptable in terms of stress level and pain but are comparatively slow.

TABLE 1

| Processing method | Response | | | |
|---|---|---|---|---|
| | total | weak | medium | strong |
| cutting | 50 | 28 | 17 | 5 |
| boiling | 50 | 21 | 19 | 10 |
| ripping/heat | 50 | 16 | 20 | 14 |

The state of the art relies on freezing techniques involving either shock-freezing by liquid nitrogen or freezing larvae at −20° C., which is a slightly slower process than shock-freezing.

While both are lethal and do not evoke behaviour that would indicate pain or stress, they, however, are very energy intensive.

FIG. 1 shows the hormonal stress response of black soldier fly larvae measured in OCT concentration following cooling processes at different temperatures and time periods and the respective recovery. The graphic shows that cooling the animals and thereby stopping their metabolism results in low octopamine levels, but a full recovery is achieved when their temperature is raised back to room temperature. The cooling process is thus fully reversible and does not harm the animals.

Further research showed that stunning or anaesthetising the animals, respectively, by cooling or gassing both lead to a decrease in stress level, whereby cooling is preferred since it acts faster and yields better results. Therefore, anaesthetising the animals before processing them is recommended. Storage in cold water did not impose additional stress to the insect larvae but slightly lowered OCT concentration. Thus, water can be used both for storing and for anaesthetising insect larvae. When processing the animals, fast methods such as cutting or shock-freezing are recommended since they do not increase the stress level as much as methods involving heat.

Thus, a processing method for appropriate inactivation of the animals with minimal stress should consider the above presented results.

The method according to the invention involves anaesthetising the insect larvae by cooling them, followed by inactivation the insect larvae by cutting, thereby destroying their nervous system.

The cooling step may be performed by mixing water with larvae. The water/insect larvae mixture may thereby have a ratio of 50:50 or may have any other suitable ratio.

Preferably, the target temperature of the cooling process is be 15° C. or lower. The target temperature of the cooling process may also be 10° C., 7° or lower.

In a preferred embodiment, the cutting process may cut each insect larva in at least 5 pieces at once. The insect larvae may be processed to protein powder thereafter.

By using a method as specified in the claims, an appropriate procedure of processing insect larvae is presented. After anaesthetising the larvae via cooling below at least about 15° C., the insect larvae are separated from rearing residue, e.g. by sieving or a washing step. A fast and efficient cutting technique leads to an immediate deactivation of the insect larvae. Furthermore, the presented method is significantly less cost and energy intensive since the freezing step is replaced by anaesthesia by cooling and successive cutting. By performing cooling and inactivating of the insect larvae, two objectives can be achieved. Firstly, the animal welfare is ensured since the process involves anaesthesia and a quick destruction of the nervous system. Secondly, the product quality is consistent since the current status of the insect larvae is preserved by cooling them and thereby stopping their metabolism.

The method may also be applied for living insects of all life cycle stadia.

The invention claimed is:

1. A method of processing insect larvae comprising the steps of:
   anaesthetising the insect larvae by cooling, wherein the insect larvae are stored in cold water before or after the anaesthetising step, followed by
   cutting the insect larvae into pieces to effect destruction of a nervous system of the insect larvae while the insect larvae are anaesthetized.

2. The method according to claim 1, wherein the insect larvae are cooled by mixing them with a fluid.

3. The method according to claim 2, wherein a cooling temperature of the fluid is below 15° C.

4. The method according to claim 2, wherein a cooling temperature of the fluid is below 7°.

5. The method according to claim 1, wherein a cooling temperature of the insect larvae is below 15° C.

6. The method according to claim 1, wherein a cooling temperature of the insect larvae is below 10° C.

7. The method according to claim 1, wherein cutting the insect larvae into pieces comprises cutting at least 90% of the insect larvae into at least 5 pieces each.

8. The method according to claim 1, wherein the insect larvae are processed to powder comprising protein and/or fat and/or chitin.

9. The method according to claim 1, wherein the insect larvae are separated from rearing residue before the anaesthetising step.

10. The method according to claim 1, wherein during storing, the insect larvae are agitated.

11. A system for processing insect larvae according to claim 1 comprising
    means for cooling the insect larvae, and
    means for cutting the insect larvae,
    wherein the system is also configured to store and cool the insect larvae in cold water before processing.

12. The system according to claim 11, wherein the cooling means are configured to maintain a temperature below 15° C.

13. The system according to claim 11, wherein the insect larvae are separated from rearing residue by separating means.

14. The system according to claim 11, wherein the cutting means are configured to cut the insect larvae in at least 5 pieces at once.

15. The system according to claim 11, wherein the system is configured to agitate the insect larvae during storing.

16. The system according to claim 11, wherein the cooling means are configured to maintain a temperature below 10° C.

17. The method according to claim 1, wherein the insect larvae are cooled by mixing them with water.

18. The method according to claim 1, wherein a cooling temperature of the insect larvae is below 7°.

* * * * *

UNITED STATES PATENT AND TRADEMARK OFFICE
CERTIFICATE OF CORRECTION

| | |
|---|---|
| PATENT NO. | : 11,930,803 B2 |
| APPLICATION NO. | : 15/734247 |
| DATED | : March 19, 2024 |
| INVENTOR(S) | : Kees Wilhelmus Petrus Aarts et al. |

It is certified that error appears in the above-identified patent and that said Letters Patent is hereby corrected as shown below:

In the Claims

Column 5, Line 20, Claim 4, delete "7°." and insert -- 7° C. --

Column 6, Line 29, Claim 18, delete "7°." and insert -- 7° C. --

Signed and Sealed this
Fourteenth Day of May, 2024

*Katherine Kelly Vidal*

Katherine Kelly Vidal
*Director of the United States Patent and Trademark Office*